United States Patent [19]

Zuckerman

[11] Patent Number: 5,720,613
[45] Date of Patent: Feb. 24, 1998

[54] REUSABLE PLASTERLESS DENTAL ARTICULATOR WITH DISPOSABLE CAST MOUNTING PLATFORMS

[76] Inventor: Gabriel R. Zuckerman, 1199 Fifth Ave., East Northport, N.Y. 11731

[21] Appl. No.: 648,284

[22] Filed: May 15, 1996

[51] Int. Cl.$^6$ ................................................. A61C 11/02
[52] U.S. Cl. ................................................. 433/63
[58] Field of Search ........................ 433/54, 57, 60, 433/61, 62, 63, 65

[56] References Cited

U.S. PATENT DOCUMENTS

| | | | |
|---|---|---|---|
| 613,772 | 11/1898 | Moffitt | 433/57 |
| 1,324,319 | 12/1919 | O'Keefe | 433/63 |
| 2,592,288 | 4/1952 | Johnson | 433/65 |
| 3,078,577 | 2/1963 | Prentki | 433/60 |
| 3,930,312 | 1/1976 | Daub. | |
| 4,207,677 | 6/1980 | Lampert | 433/60 |
| 4,252,523 | 2/1981 | Gayso | 433/60 |
| 4,412,822 | 11/1983 | Blechner | 433/60 |
| 4,619,611 | 10/1986 | Shimbashi | 433/54 |
| 4,854,868 | 8/1989 | Pitre | 433/60 |
| 5,007,829 | 4/1991 | Farrell | 433/54 |
| 5,046,949 | 9/1991 | Richardson | 433/57 |

*Primary Examiner*—Cary E. O'Connor
*Attorney, Agent, or Firm*—Collard & Roe, P.C.

[57] ABSTRACT

A dental articulator and method for manufacturing same for properly positioning upper and lower dental casts relative to each other. Upper and lower brackets are provided which accommodate disposable platforms that are permanently adhered to the casts. A coupling plate is removably coupled to one of the brackets for pivotal movement therebetween about a first axis. The coupling plate is removably coupled to the other bracket for pivotal movement therebetween about a second axis perpendicular to the first axis. The coupling plate also provides sliding movement with respect to the other bracket for adjusting a distance between the brackets. The brackets and coupling plates are made from a metal having sufficient rigidity so that, even upon repeated assembly and disassembly, an accurate bite relationship between the upper and lower dental casts is repetitively reproduced. In manufacturing the articulator, the two brackets and coupling plates are stamped or cut from sheet metal. Extensions of the brackets are folded to form supports for the brackets and the coupling assembly. The disposable platforms are extrusion molded from plastic.

15 Claims, 2 Drawing Sheets

REUSABLE PLASTERLESS DENTAL ARTICULATOR WITH DISPOSABLE CAST MOUNTING PLATFORMS

FIELD OF THE INVENTION

This invention relates to a reusable dental articulator with disposable cast mounting platforms. Upper and lower dental casts are secured to the instrument with adhesive, instead of the move conventional method, which employs plaster of paris a connecting material. The invention also relates to a method for manufacturing the dental articulator and the platforms.

THE PRIOR ART

An articulator is a mechanical jaw joint. Replicas of the patient's jaws and teeth, the dental casts, are attached to the articulator for the purpose of fabricating a dental prosthesis, appliance, or other apparatus. These instruments are capable of accepting bite relation records, and will reproduce the bite relationship of the attached casts when they are in the closed position. When the articulators are in the open position, the casts are accessible for inspection and to permit technical procedures to be performed, which are required to produce dental appliances and prostheses.

Articulators for dental casts are well known and have been used for many years. An example of two prior art articulators may be found in U.S. Pat. No. 3,930,312 and U.S. Pat. No. 5,046,949. The prior art articulators generally fall into two categories; disposable and reuseable articulators.

Dental laboratories using disposable articulators must use a new articulator for each prosthesis they construct. For a commercial dental laboratory, an inventory of these items represents a significant investment and requires substantial storage space. The disposable articulators currently available are constructed from flexible, plastic materials and lack the rigidity required to repetitively reproduce an accurate bite relationship during use.

Reusable articulators generally have the dental casts attached directly onto the articulator brackets using plaster of paris as a coupling agent. This method of attachment is a time consuming, messy process. The high quality reusable plasterless articulators are too expensive for high production in a commercial dental laboratory.

This invention does not require plaster of paris to join the upper and lower dental casts to the articulator. Casts are secured, with an adhesive, to disposable mounting platforms, which clip or slide onto the upper and lower brackets of the articulator. The casts are removed from the articulator, when the technical work has been completed, by sliding them off together with the attached mounting platforms. This procedure leaves the articulator clean and ready for reuse with another set of dental casts.

SUMMARY OF THE INVENTION

It is therefore an objective of the present invention to provide a reusable dental articulator for use with inexpensive, disposable platforms to which the dental casts can be fastened with adhesive.

It is a further objective of the present invention to provide a dental articulator which can be manufactured and sold at a reasonable cost.

It is yet another objective of the present invention to provide a dental articulator capable of assuming several convenient positions and configurations. These positions and configurations provide access to the dental casts so that the technical procedures required to produce dental prostheses and appliances may be performed.

This articulator is capable of accepting any set of casts which have been prepared so that their bases are flat and reasonably parallel to one another when occluded. The articulator can be adjusted to accommodate casts when their bases are slightly divergent and the combined height of the occluded casts varies. The upper and lower dental casts are cemented to disposable mounting platforms placed on the upper and lower brackets of the instrument with an adhesive, such as cyanoacrylate. The disposable mounting platforms with the attached casts can be easily removed and accurately replaced on the instrument. This arrangement allows the articulator to be reused with other sets of dental casts.

The articulator is constructed from five (5) parts: an upper bracket, a coupling plate, a lower bracket, and upper and lower mounting platforms, which are identical in size and shape. The lower bracket and the coupling plate are held together by a carriage bolt, washer and wing nut. The remaining parts interlock with one another to complete the assembly.

The lower metal bracket has a three point support for the articulator in the upright position and a vertical support for connection with the coupling plate, described below. There is a square hole in the vertical support to contain the square neck of a carriage bolt.

The planar metal coupling plate has laterally formed hinge pins and a vertical slot. An adjustable, rotating connection is formed between the lower bracket and the coupling plate by the carriage bolt, which passes through the square hole in the lower bracket's vertical support and through the slot in the coupling plate. The connection can be secured in any position along the slot by tightening the wing nut over the washer on the end of the carriage bolt.

The upper metal bracket has a three point support for the articulator in the inverted position and two vertically formed hinge arms. There are holes in the lower end of the hinge arms into which the hinge pins of the coupling plate fit. A hinge mechanism is formed when the hinge arms of the upper bracket contain the hinge pins of the coupling plate. The hinge arms are sufficiently elastic to allow them to be spread apart, to engage and release the hinge pins from the holes at their lower ends. In this manner, the upper arm can be attached to, and removed from, the lower section of the articulator.

The configuration of the assembly, thus far described, creates two horizontal axes of rotation, which are perpendicular to one another. The first axis of rotation passes through the hinge pins of the coupling plate and the holes into which they fit in the upper bracket. A second axis of rotation passes through the long axis of the carriage bolt, which joins the coupling plate to the lower bracket. This connection can rotate and slide, to increase or decrease the distance between the upper and lower brackets. These features allow the articulator to accommodate different sets of occluded dental casts of varying heights, which have bases that are parallel to, or moderately divergent from, one another. The first axis of rotation also allows the articulator to be opened 180° to create access to the dental casts casts the technical procedures required to fabricate dental prosthesis and appliances. The width and configuration of the upper and lower brackets provide a defined and secure seat for the mounting platforms, which clip or slide into place.

The upper and lower brackets and the coupling plate are manufactured by cutting, die cutting or laser cutting sheet metal to shape. The upper and lower brackets are then folded into their final configuration. The disposable mounting platforms are designed to be extrusion molded, after which they are cut into short sections.

BRIEF DESCRIPTION OF THE DRAWINGS

Other objects and features of the present invention will become apparent from the following detailed description, when considered in connection with the accompanying drawings. It is to be understood that the drawings are designed as an illustration only, and not as a definition of the limits of the invention.

In the drawing, similar numbers identify similar elements throughout the several views.

DETAILED DESCRIPTION OF THE PREFERRED EMBODIMENT

Figure 1:
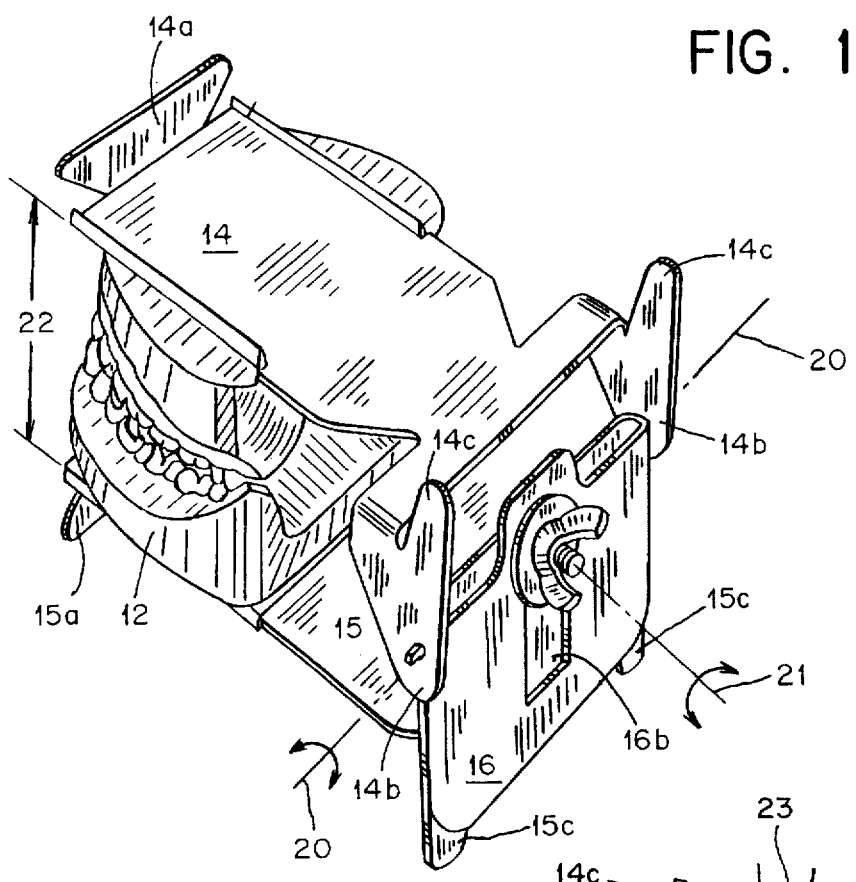
FIG. 1 is a perspective view of the dental articulator, according to the invention, in the closed position.

FIGS. 1 through 4 illustrate the dental articulator, according to the invention.

Upper and lower dental casts 11 and 12 are secured to their respective mounting platforms 13 with adhesive. The mounting platforms 13 are removably positioned on the upper bracket 14 and the lower bracket 15 of the articulator. A coupling plate 16 is connected to the vertical support 15b of the lower bracket 15 by a carriage bolt 17, washes 18 and wing nut 19.

The upper metal bracket 14 has a front extension, which is folded upward 90° to create the upper front leg 14a of the articulator. The lateral extensions of the upper bracket are folded downward 90° to produce the hinge arms 14b and the upper back legs 14c. The hinge pins 16a of the coupling plate 16 fit into the holes 14d in the lower end of the hinge arms 14b. The dimensions 14e of the upper bracket provides a secure rim to engage the opposing flanges 13a of the upper mounting platform 13. The shoulders 14f of the upper bracket define the posterior limits of the seat for the upper mounting platform.

The planar metal coupling plate 16 has laterally formed hinge pins 16a, which fit into the holes 14d in the hinge arms 14b. A vertical slot 16b in the coupling plate creates the expandable feature of the connection between the coupling plate 16 and the vertical support 15b of the lower bracket The lower metal bracket 15 has a front extension which is folded downward 90° to create the lower front leg 15a of the articulator. The posterior extension of the lower bracket 15, is folded upward 90° to produce a vertical support 15b above and two lower back legs 15c beneath the articulator vertical support 15b has a square hole 15d to engage the square neck of carriage bolt 17. The dimension 15e of the lower bracket 15 provides a secure rim to engage the opposing flanges 13a of the lower mounting platform 13. Shoulders 15f on the lower bracket 15 define the posterior limit of the seat for the lower mounting platform 13.

Figure 2:
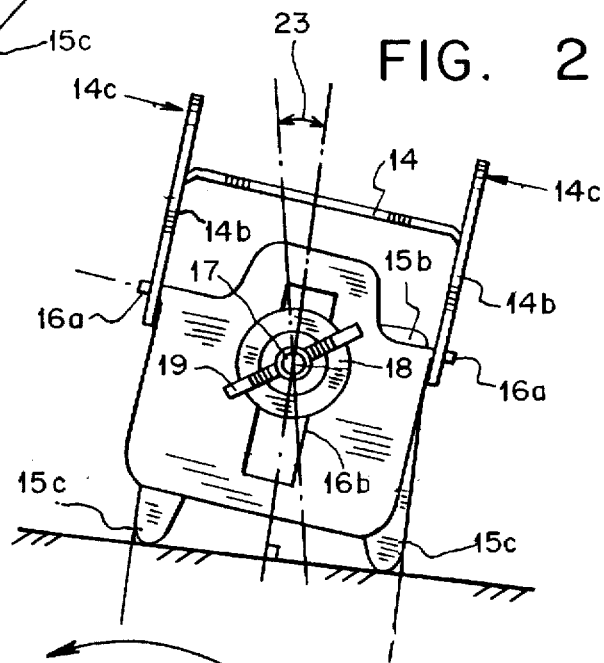
FIG. 2 is a rear elevation view of the dental articulator.

The configuration of the articulator provides one vertical and two rotational ranges of adjustment. This feature makes it possible to mount a variety of occluded casts of varying heights which have bases that are parallel or slightly divergent from each other. Rotation around axis 20 provides adjustment for casts when their bases are divergent in the sagittal plane. FIG. 2 illustrates clockwise rotation 23 of the upper bracket around axis 21 to provide adjustment for casts when their bases are divergent in the frontal plane. Vertical height adjustment is made by sliding the coupling plate 16 up or down along the vertical slot 16b, thereby increasing or decreasing the distance 22 between the upper and lower brackets. Once proper alignment of the upper bracket with the upper cast is achieved, the carriage bolt 17, and wing nut 19 are tightened, securing the connection in the desired position. Once the articulator has been adjusted for a particular set of casts, the casts may be fastened to the mounting platforms on the instrument with adhesive 24.

Figure 4:
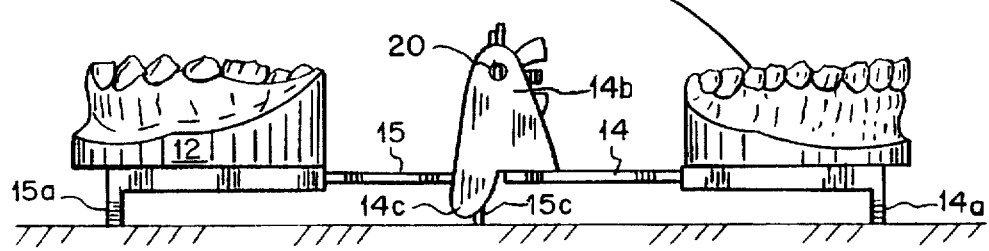
FIG. 4 is a left side elevation view of the dental articulator in the open position.

FIGS. 1 and 4 show the articulator in the closed and open positions, respectively. The articulator is capable of assuming these positions by rotating the upper bracket 14 180° around axes 20. This arrangement allows the technician to conveniently change the configuration of the articulator to those shown in FIGS. 1 and 4. A third position, in which the upper bracket is separated from the articulator, can also be conveniently produced. The upper bracket 14 may be removed from the coupling plate 16 by stretching the hinge arms 14b apart to disengage the hinge pins 16a. Replacing the hinge arm 14b of the upper bracket 14 on the hinge pins 16a restores the original setting. In this way, access to the dental casts is conveniently achieved which is required to perform the technical procedures necessary to produce dental prostheses and appliances.

Figure 3:
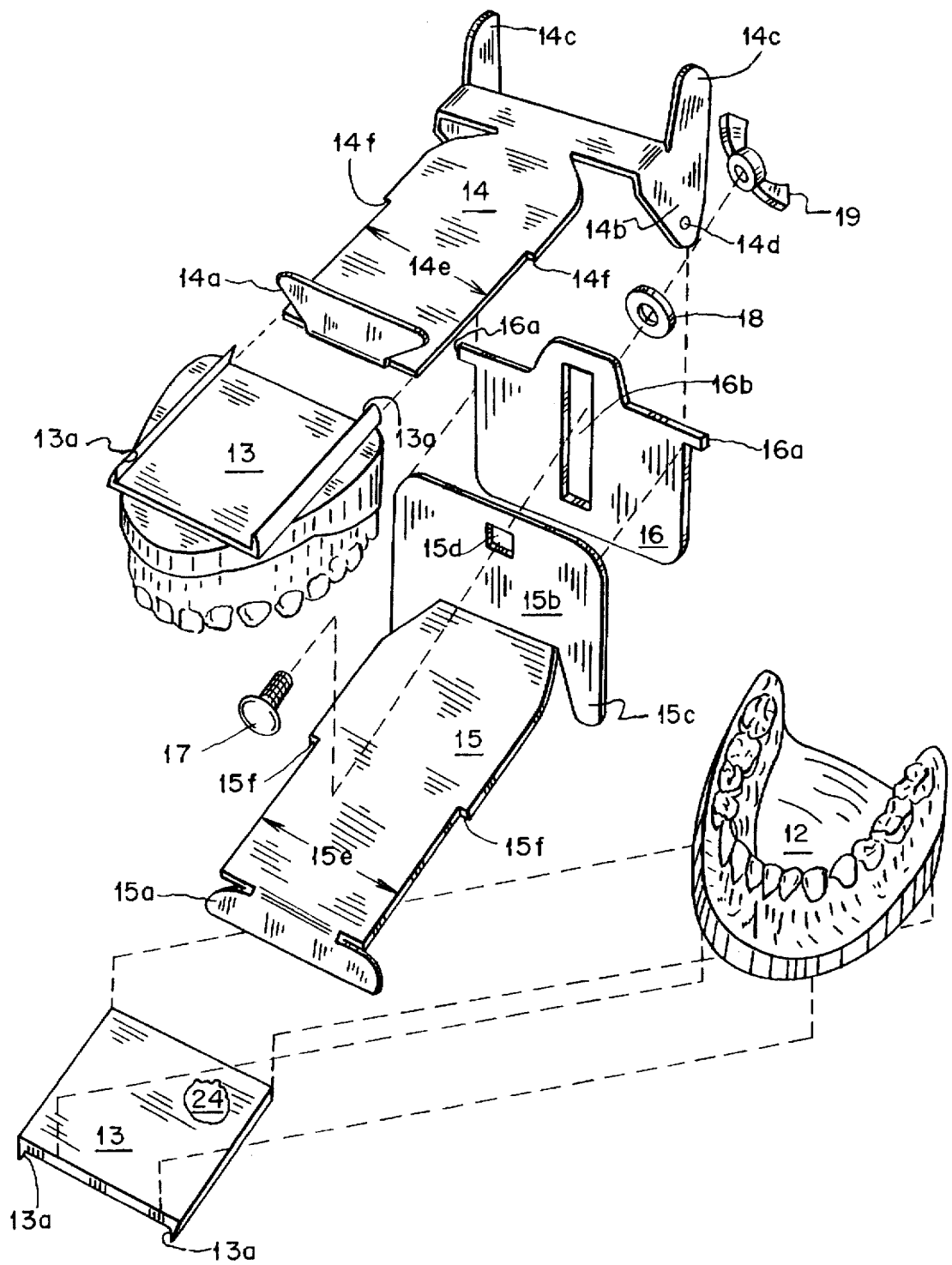
FIG. 3 is an exploded view of the dental articulator showing the various constructional components.

FIG. 3 shows a pair of disposable mounting platforms extrusion molded from plastic. The platforms slide on brackets and 15 until they contact shoulders 14f and 15f. This arrangement insures that the mounting platforms, with their attached casts, can always be removed and replaced on the articulator in the same position.

The mounting platforms 13 are square plastic plates with flanges 13a formed on two opposite edges. The size and shape of the flanges, and the material from which the platforms are made, produces a unit which is slightly elastic. When the mounting platforms 13 are installed on the upper and lower brackets, the flanges 13a firmly engage the edges of the bracket seats 14e and 15e. The design of the mounting platforms formed in this manner produce a secure, and removable, attachment with the upper bracket 14 and lower bracket 15 of the articulator. The dental casts 11 and 12 are cemented onto the mounting platforms 13. Any appropriate adhesive can be used to secure casts to the mounting platforms. Cyanoacrylate adhesive is recommended because of its fast cure time and the tenacious bond it creates between the gypsum dental casts and the plastic mounting platforms. Each cast requires a mounting platform when it is cemented on the articulator. Platforms 13 are readily removed from the articulator brackets 14 and 15, by sliding them forward, off the instrument.

Accordingly, while only one embodiment of the present invention has been shown and described, it is obvious that many changes and modifications may be made thereunto without departing from the spirit and scope of the invention.

What is claimed:

1. A dental articulator for supporting and properly positioning upper and lower dental casts relative to each other comprising:

an upper and a lower bracket adapted for the removable attachment thereto of the upper and lower dental casts, respectively;

a coupling plate removably hinged to said upper bracket for rotation about a first axis; and a coupling axle with securing means for demountably locking said coupling plate to said lower bracket forming a vertical sliding connection, said coupling plate being pivoted with respect to said lower bracket about said coupling axle.

2. The dental articulator according to claim 1, wherein the brackets and the coupling plate are made from sheet metal, which is sufficiently rigid to create a reliable articulator sufficiently flexible to be folded without cracking or breaking, and sufficiently elastic to be stretched apart without creating permanent distortion.

3. The dental articulator according to claim 1, wherein said lower bracket includes a three-point support for the articulator in an upright position and said upper bracket includes a three-point support for the articulator in an inverted position.

4. The dental articulator according to claim 1, wherein said coupling plate includes hinge pins and wherein said upper bracket includes a pair of hinge arms for engaging the hinge pins of said coupling plate.

5. The dental articulator according to claim 4, wherein said sliding connection is formed by a slot in said coupling plate, with said coupling axle extending through the slot for adjusting the space between said brackets.

6. The dental articulator according to claim 1, comprising disposable mounting platforms slidably and detachably received on each of said upper and lower brackets and adapted for attachment to each of the upper and lower dental casts.

7. The dental articulator according to claim 6, wherein each of said upper and lower brackets include a seat for receiving and demountably securing each mounting platform in a defined predetermined position.

8. The dental articulator according to claim 7, wherein said seat includes shoulders for defining the posterior limits of the position of each of said mounting brackets.

9. A method for manufacturing a dental articulator for supporting and positioning upper and lower dental casts comprising the steps of:

shaping a sheet metal plate to make a lower bracket and having a seat for supporting the lower dental cast, said lower bracket including a vertical support having a connection hole;

shaping a sheet metal plate to make an upper bracket having a seat for supporting an upper dental cast, and a pair laterally-disposed vertical hinge arms;

forming the metal plate of said lower bracket to create three-point support for the articulator in an upright position, and a vertical support;

forming the metal plate of said upper bracket to create a three-point support for the articulator in the inverted position;

shaping a sheet metal coupling plate with a slot and extensions to form hinge pins for coupling to the vertical hinge arms of said upper bracket, and connecting said coupling plate through its slot to the hole in vertical support of said lower bracket.

10. The method according to claim 9, wherein each sheet metal plate is shaped by cutting the sheet metal material.

11. The method according to claim 9, wherein each sheet metal plate is shaped by laser cutting the sheet metal material.

12. The method according to claim 9, wherein each sheet metal plate is shaped by die cutting the sheet metal material.

13. The method according to claim 9, whereby the parts of the articulator are assembled by joining said coupling plate to said lower bracket with a carriage bolt, washer and wing nut; and connecting said upper bracket by inserting the hinge pins of said coupling plate into holes formed in the lower end of said upper bracket's hinge arms.

14. The method according to claim 9, further comprising the step of extrusion molding thin, flat, square disposable plastic mounting platforms, having flanges on two opposing edges for demountably coupling to the seat of each of said brackets.

15. The method according to claim 14, wherein the disposable plastic platforms are adapted for adhesive attachment to the dental casts.

* * * * *